United States Patent [19]
Goldstein

[11] Patent Number: 5,515,851
[45] Date of Patent: May 14, 1996

[54] ANGIOGRAPHIC FLUID CONTROL SYSTEM

[76] Inventor: James A. Goldstein, 7260 Creveling, St. Louis, Mo. 63130

[21] Appl. No.: 99,416

[22] Filed: Jul. 30, 1993

[51] Int. Cl.$^6$ ..................................................... A61B 6/00
[52] U.S. Cl. ........................... 128/654; 128/656; 128/658; 604/27; 604/30; 604/67; 604/284
[58] Field of Search ................................ 128/654, 656, 128/658, 653.1, 4, 6; 600/3, 118, 131; 604/27, 28, 30, 36, 53, 67, 65, 93, 264, 280, 284

[56] References Cited

U.S. PATENT DOCUMENTS

| | | | |
|---|---|---|---|
| 4,006,736 | 2/1977 | Kranys et al. | 128/655 |
| 4,090,502 | 5/1978 | Tajika | 128/654 |
| 4,402,310 | 9/1983 | Kimura | 604/30 |
| 4,552,130 | 11/1985 | Kinoshita | 604/27 |
| 4,585,941 | 4/1986 | Bergner | 128/654 |
| 4,781,687 | 11/1988 | Wall | 604/151 |
| 4,836,187 | 6/1989 | Iwakoshi et al. | 128/4 |
| 4,844,052 | 7/1989 | Iwakoshi et al. | 128/4 |
| 4,854,301 | 8/1989 | Nakajima | 128/4 |
| 4,954,129 | 9/1990 | Giuliani et al. | 604/53 |
| 5,108,365 | 4/1992 | Woods, Jr. | 604/53 |
| 5,133,336 | 7/1992 | Savitt et al. | 128/4 |
| 5,191,878 | 3/1993 | Iida et al. | 128/4 |
| 5,242,390 | 9/1993 | Goldrath | 128/4 |
| 5,269,756 | 12/1993 | Dryden | 604/151 |
| 5,301,656 | 4/1994 | Negoro et al. | 128/4 |

OTHER PUBLICATIONS

Reduction of Radiation Exposure to the Cardiologist During Coronary Angiography by the Use of a Remotely Controlled Pump for injection of Contrast Medium; Grant; Catheterization & Cardiovascular Diagnoses 25:107–109 (1992).

Remote Hydraulic Syringe Actuator; Dardib Arch Surg 115:105 (1980).

Power Injection of Contrast Media During Percutaneous Transluminel Coronary Artery Angioplasty; Goss. Catheterization & Cardiovascular Diagnosis 16:195–198 (1989).

Use of Mechanical Injectors During Percutaneous Transluminal Coronary Angioplasty (PTCA); Angelini; Catherization & Cardiovascular Diagnosis 16:193–194 (1989).

Safety & Convenience of a Mechanical Injector Pump for Coronary Angiography; Ireland; Catherization & Cardiovascular Diagnosis 16:199–201 (1989).

Selective Coronary Angiography Using a Power Injector; Gardiner AJR 146:831–833 Apr. 1986.

$CO_2$ Power–Assisted Hand–held Syringe; Krieger Catheterization and Cardiovascular Diagnosis 19:123–128 (1990).

Primary Examiner—Krista M. Zele
Assistant Examiner—Brian L. Casler
Attorney, Agent, or Firm—Neal Kalishman

[57] ABSTRACT

A system and method for injecting fluids during angiographic procedures. A finger activated control pad is used to regulate the injection of fluids by a single operator who simultaneously manipulates the primary catheterization equipment.

9 Claims, 6 Drawing Sheets

ANGIOGRAPHIC FLUID CONTROL SYSTEM

BACKGROUND OF THE INVENTION

Invasive contrast angiography, the x-ray visualization of various body organs via injection of contrast dye delivered through catheters advanced into selected target organs, is widely employed in the evaluation of a variety of medical disorders. Though the techniques employed to perform contrast studies of various vascular beds and organs may vary according to the target, there are many technical and operational issues with regard to both methods and devices that are common to nearly all such angiographic procedures. These include: (1) access devices, which serve as the route of entry into the organ and/or vascular space in general; (2) diagnostic and guiding catheters, which serve to access the specific organ/circulation to be studied [these catheters are typically preformed in specific shapes and sizes designed to access each specific organ/circulation (coronary, cerebral, renal, etc.)]; (3) guide wires, which serve to safely and efficiently facilitate positioning of angiographic and interventional catheters at the target circulation; (4) an angiographic manifold, connected to the back end of the angiographic catheter, which serves to facilitate administration of procedure dependent fluids (saline, contrast dye, certain drugs, etc.); this manifold may contain anywhere from 2–4 (or occasionally more) ports with stopcocks. These ports are typically connected to flexible tubing which lead to reservoirs of procedure dependent fluids (e.g. contrast dye, saline, etc. ). The back end of the manifold is typically connected to a contrast injection system (either directly or indirectly), which allows administration of the contrast dye (the medium by which angiographic pictures of the target organ are made); contrast dye may be injected through a hand controlled syringe attached to the manifold (either directly or via flexible tubing); alternatively, the injection system may consist of a power injector which is similarly connected to the manifold by plastic tubing.

Many angiographic procedures, in particular coronary angiography and especially coronary vascular interventional procedures such as angioplasty, require frequent intermittent injections of contrast dye. Contrast dye is administered in varying volumes as well as modulated strengths and durations of injection. Intermittent dye injections are critical for optimal positioning of guiding catheters at the target vessels, positioning of guide wires to and through the target areas during catheter interventions (e.g. percutaneous transluminal coronary angioplasty) and for assessment of the results of such interventional procedures.

At present, angiographic procedures are typically performed employing a hand held syringe injector for most contrast injections. However, throughout such procedures there is a requisite need for ongoing and often constant manipulation, adjustment and control of the various catheterization devices (guiding catheter, coronary guide wire and balloon dilatation catheter for angioplasty and sometimes even the vascular access sheath itself), above and beyond the syringe injection system itself. As presently performed, the procedural demands for manipulation of devices precludes one individual operator from simultaneously controlling and manipulating the procedure dependent devices, as well as injecting the contrast dye necessary to perform such complex procedures. At present, in the case of a single operator, such procedures therefore require cumbersome and inefficient juggling of devices. To avoid these inefficiencies and attendant suboptimal procedural performance, most procedures require at least two personnel: (1) The primary procedural operator, always a physician (radiologist, cardiologist or surgeon), who is responsible for control and manipulation of the sheaths, guiding catheters, guide wires and balloon dilatation catheters; and (2) an associate operator (another physician, nurse or a technician) who will act as a first assistant, with main responsibility of injecting dye at the order of the primary operator. This system is not only inefficient from the standpoint of utilization of personnel, but may limit procedural quality and efficiency. That is, the assistant, whose primary role is injecting dye, may not possess the general background, moment-to-moment insights nor have the expertise to deliver the desired volume, rate and duration of contrast at precisely the times the primary operator so desires. Therefore, there is a need for an angiographic system that would facilitate performance of such procedures by a single operator. That is, a device (or devices) that would allow the primary operator to both simultaneously manipulate the various procedure dependent devices (sheaths, catheters and wires) and inject procedure dependent fluids (angiographic contrast).

SUMMARY OF THE INVENTION

An angiographic fluid control system and method which comprises a catheter, at least one fluid reservoir, a manifold in communication with said catheter and reservoir for passage of fluids and devices, a pumping device for injecting fluids from said reservoir through said manifold, and a control unit which communicates with said pumping device wherein said control unit has a communications pad that is activated by an operator's fingers for the precise injection of fluids.

DESCRIPTION OF PREFERRED EMBODIMENTS

The integrated angiographic control system of the invention is designed to allow the primary operator (angiographer/interventionalist) to perform angiographic/interventional procedures solo. The angiographic system consists of three (3) fundamental components: (1) A fluid reservoir module; (2) a multiport converging manifold; and (3) a finger touch control pad device.

The preferred fluid reservoir module consists of several integrated components including: a microprocessor, cabinets for procedure dependent fluid reservoirs, and hydraulic cuff occluders. The fluid reservoir cabinets are designed to accommodate snap-in disposable fluid reservoir syringes. The fluid reservoir cabinets contain pneumatic or electric motor driven piston-plunger systems which connect to and control fluid injection output from disposable fluid reservoirs. The fluid reservoirs are connected to uniquely designed plastic connect tubing which passes through encircling hydraulic occluder cuffs. The hydraulic occluder cuffs control the opening and closing of access from the fluid reservoirs to the catheters by compressing or decorepressing plastic connecting tubing running from the fluid reservoirs to a multiport converging manifold. This manifold consists of three ports which converge to a common channel that connects to a catheter or Y connecting device which then delivers fluid to the patient. Input to the microprocessor is derived from an angiographic control pad equipped with triggers that electronically signal the microprocessor to initiate and modulate injection of fluids. The control pad system can be clipped onto the hub of the guiding catheter, dilatation balloon, connector apparatus or manifold; alternatively, it can be mounted on a swing-out movable-height adjustable platform attached to the catheterization table, to be positioned within near proximity of the operator's hands and the other angiographic equipment. Thus, injections can be performed by a single operator, while both hands are primarily occupied in the control and manipulation of guiding catheters, guide wires and angioplasty balloons.

Figure 1:
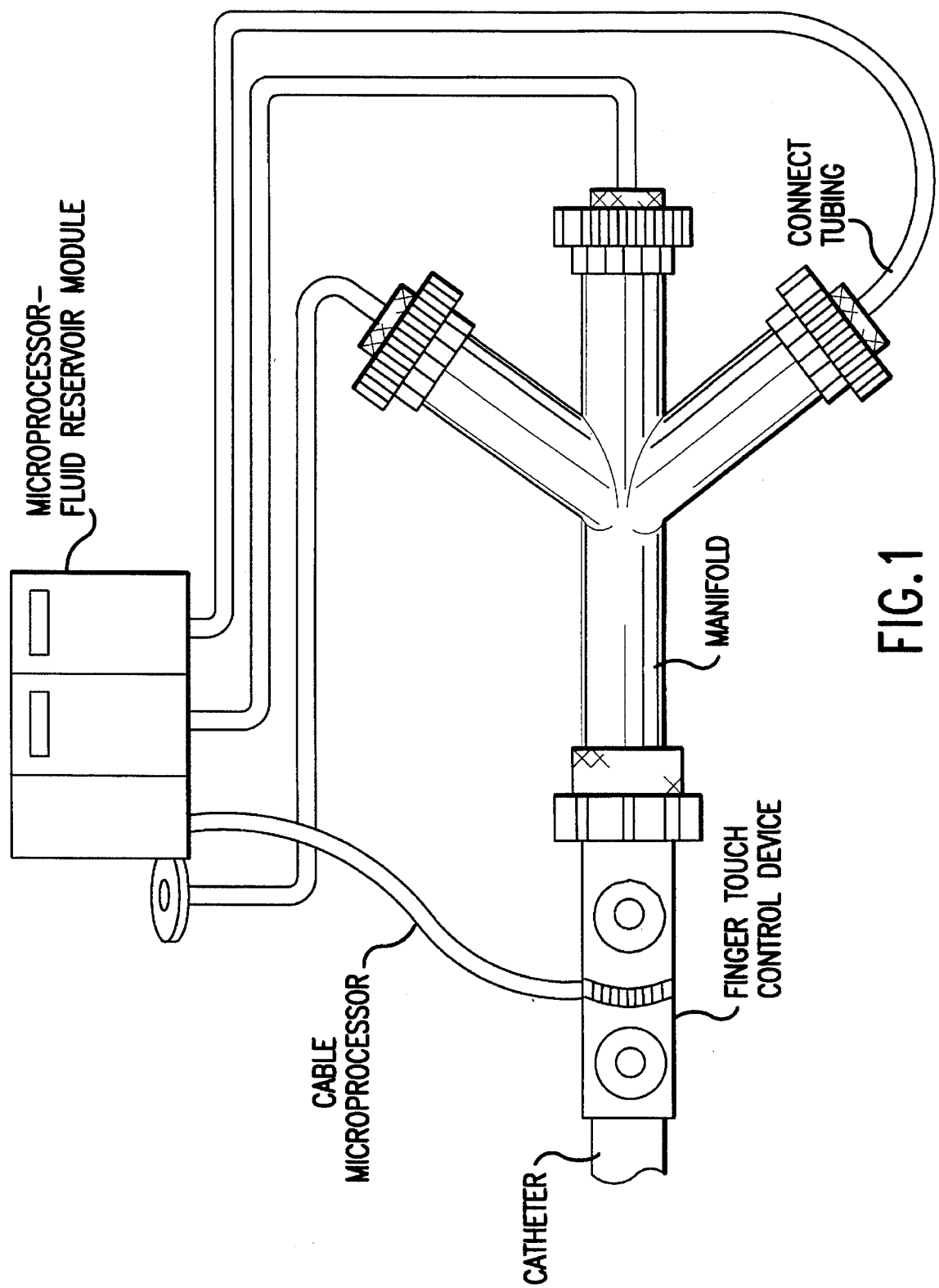
FIG. 1 shows the system of the invention.

Microprocessor Control-Fluid Reservoir Module (FIG. 1)

The angiographic system is controlled by an integrated microchip processor control-fluid reservoir module consisting of a microprocessor controller, pneumatic piston drive plungers, fluid reservoir cabinets and hydraulic cuff occluders. There is single source input to the module by cable connection from the angiographic control pad, which is detached from the module itself. There is dual output from the processor to: (a) hydraulic cuff occluders encircling connect tubing (between fluid reservoirs and manifold); and (b) pistons connected to pressure driven prepackaged syringes containing procedure dependent fluid. The pneumatic driven plunger systems are connected to and controlled by the microprocessor. These plunger systems are fully integrated and permanently attached into the fluid reservoir Cabinets. These are three (3) hydraulic occluder cuffs permanently attached and fully integrated into the microprocessor-fluid reservoir module. The module contains three (3) encircling hydraulic occluder cuffs consisting of circular plastic ring housings with circular hydraulic bladders (or circular pneumatic driven clamps). The occluder cuffs are connected to a hydraulic system contained within the module and controlled by the microprocessor. The occluders control the passage of fluid from the reservoirs to the manifold by externally compressing or decompressing the plastic connect tubing interposed between the fluid reservoirs and manifold in response to finger touch controls initiated at the angiographic pad and controlled through the microprocessor. Two hydraulic occluder cuffs are positioned at the bottom or outlet portion of the fluid reservoir cabinets and control fluid injection. The third hydraulic occluder is responsible for pressure monitor and is mounted on a swing-out support bar; during the procedure setup, the pressure monitor occluder can be swung out to allow for pressure monitor connect tubing to be passed through it to a pressure amplifier. When not in use, this occluder can be housed in a small cabinet (occluder housing) located at the lower left corner of the module. The fluid reservoir cabinets are designed to accommodate snap-in disposable fluid reservoirs that connect to the plunger system and ultimately to the manifold by plastic connect tubing. The cabinets also contain built-in fluid reservoir monitors connected to digital readout monitors located above each fluid reservoir cabinet; these monitors provide on-line readings the pressure of the pneumatic drive system, the volume and rate of fluid delivery and the remaining amount of fluid in each reservoir.

Disposable Fluid Reservoirs (FIG. 1)

Single use disposable prepackaged fluid reservoirs consist of plastic calibrated syringe-like cylinders with plungers for precision injection and uniquely designed to connect with the pneumatic driven plunger in the fluid reservoir cabinets. Alternatively, these fluid reservoirs may consist of compressible plastic bags controlled by encircling pneumatic bladders. These fluid reservoirs may contain contrast dye, saline or other procedure dependent fluids. The reservoirs connect with plastic tubing which then connect to the manifold.

Figure 2:
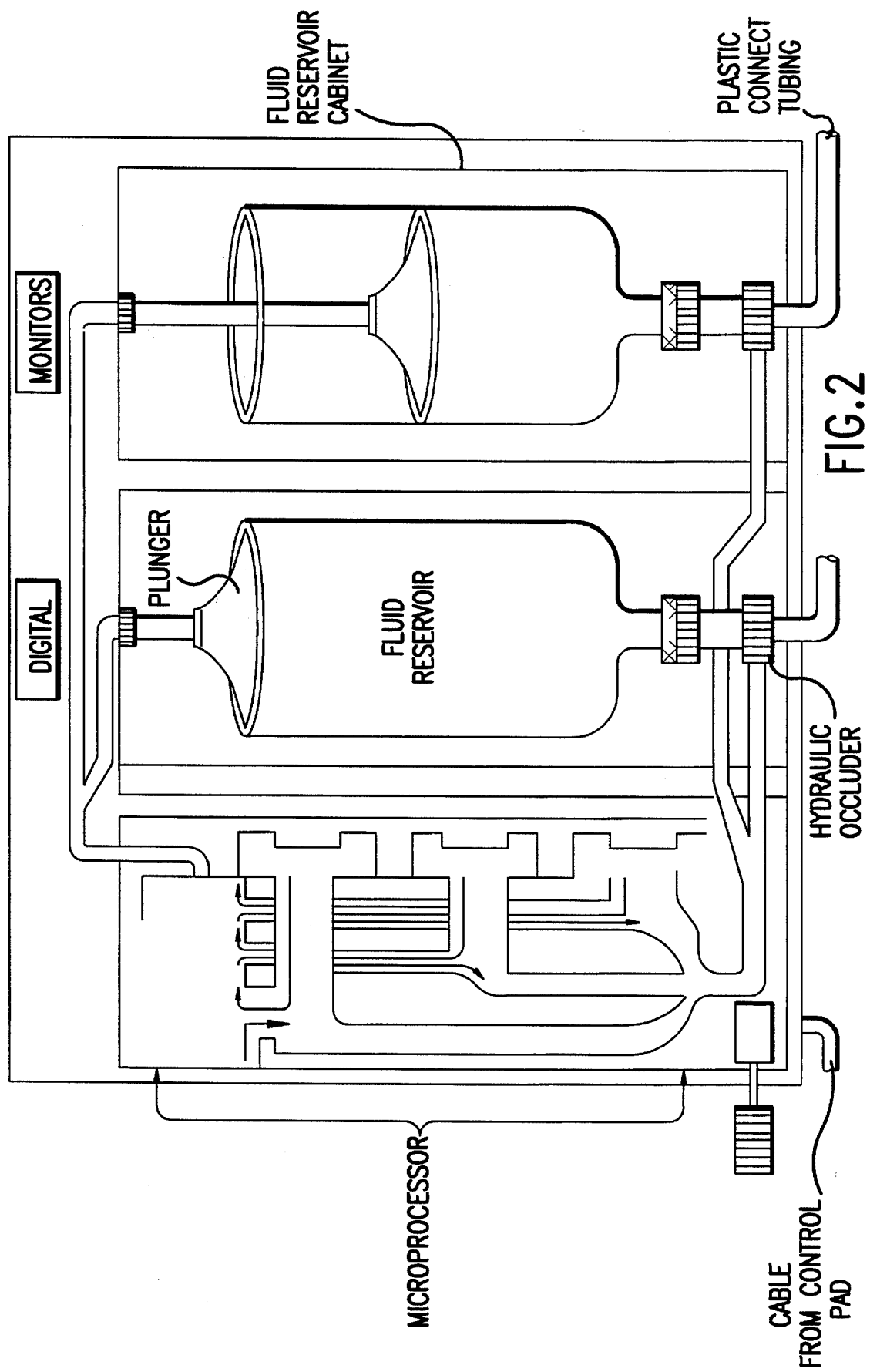
FIG. 2 shows the fluid reservoir module of the invention.

Three-Way Converging Manifold (FIG. 2)

A 3-way "Y" shaped disposable plastic manifold. The distal (or back end) of the manifold has three separate uniquely designed connector ports that are connected to specially designed high pressure disposable tubing lines with uniquely designed compatible fittings. The tubing lines are themselves connected to pressure controlled/driven reservoirs of procedure dependent fluids (contrast dye, saline, cardioplegia, etc.). The three distal ports converge into a single common channel which then exits through the proximal port connected to the guiding catheter or interventional connecting device. The proximal or front end of this device has a uniquely designed connection for attachment to the guiding catheter (or connection devices when employed for interventions). The saline flush line tubing has a 3-way stopcock interspersed at its mid point which connects to a hand controlled syringe, which serves as a "fail-safe" backup to flush the system or inject procedure dependent drugs.

Figure 3:
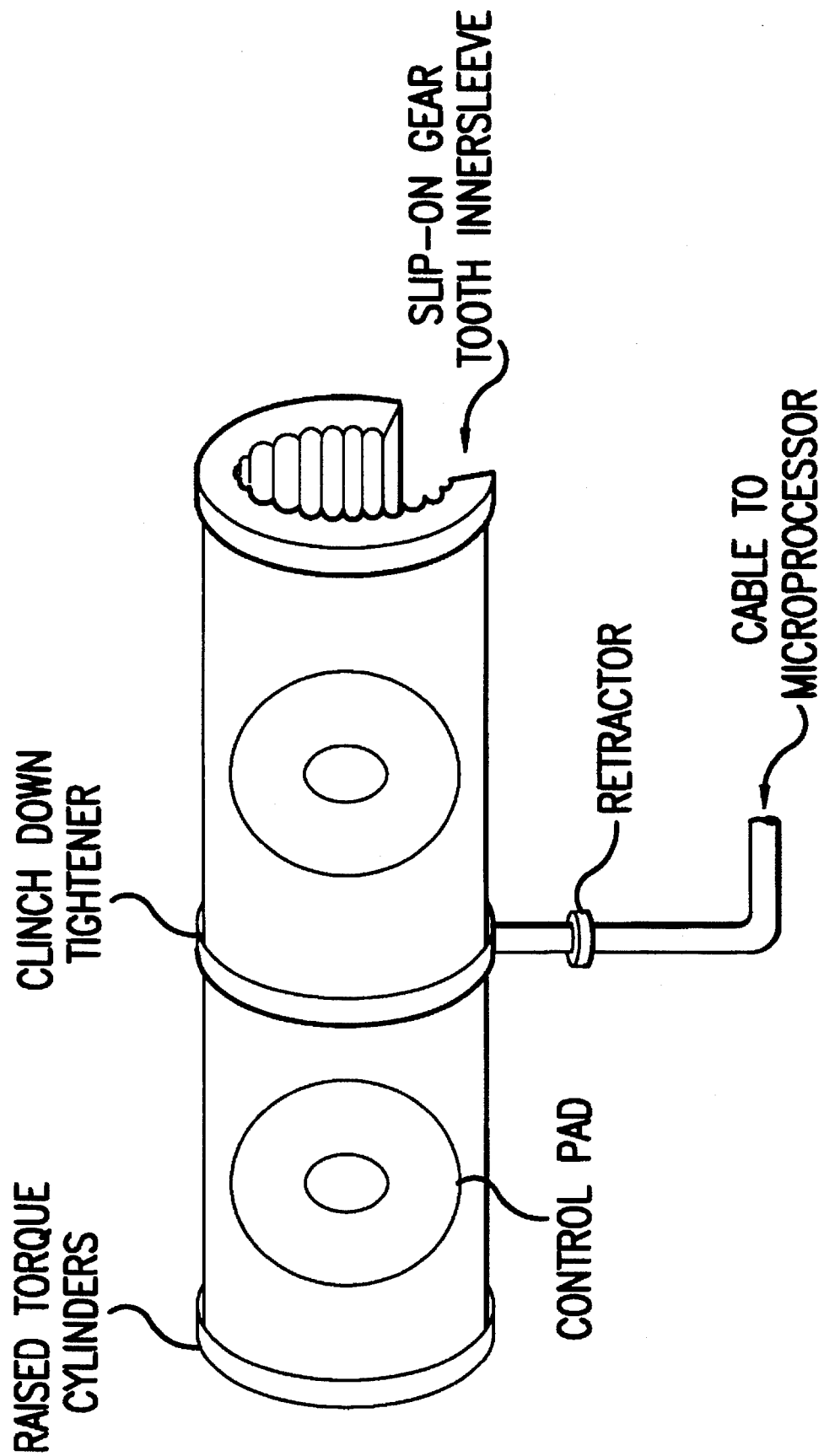
FIG. 3 shows the finger pad unit of the invention.

Angiographic Control Device (FIG. 3)

Input to the microchip control device is derived from an angiographic control pad device designed to facilitate finger touch modulation of the rate, volume and duration of injection of procedure dependent fluids (such as contrast). This angiographic control device consists of a cylindrical plastic sleeve with two control triggers (finger pads). These finger pads are integrated with electrical switches and piezo electric crystals that respond to pressure (depression) of the pad with electrical signals that are transmitted by cable connectors to the microprocessor and thereby control opening and closing of the occluder cuffs, as well as the rate and volume of injection of procedure dependent fluids. The outer surface of the sleeve has ribbed raised rings (for torque control of the catheter when this device is connected on a catheter). The trigger pads are recessed on this outer sleeve. The inner lumen of the sleeve has a fitting designed to integrate with guiding catheters or Y connector hubs; the middle raised ring has an adjustable inner clamp to tighten down and fasten the sleeve to the catheter or Y connector.

Initial depression of the pad opens one of the delivery ports, whereas further finger depression will, through servomechanism feedback controls, initiate delivery of fluid at variable rates and pressures of injection in proportional response to the duration and extent of depression of the trigger pad. The procedure dependent fluid reservoirs are pressure driven and these pressures may be variably programmed at different levels. Therefore, the combination of the activation and release maneuvers in association with the pressure of injection and caliber of tubing and manifold, will determine the ultimate volume and rapidity of injection of procedure dependent fluids. Subsequent release of the trigger will discontinue the injection and revert the port openings.

Figure 4:
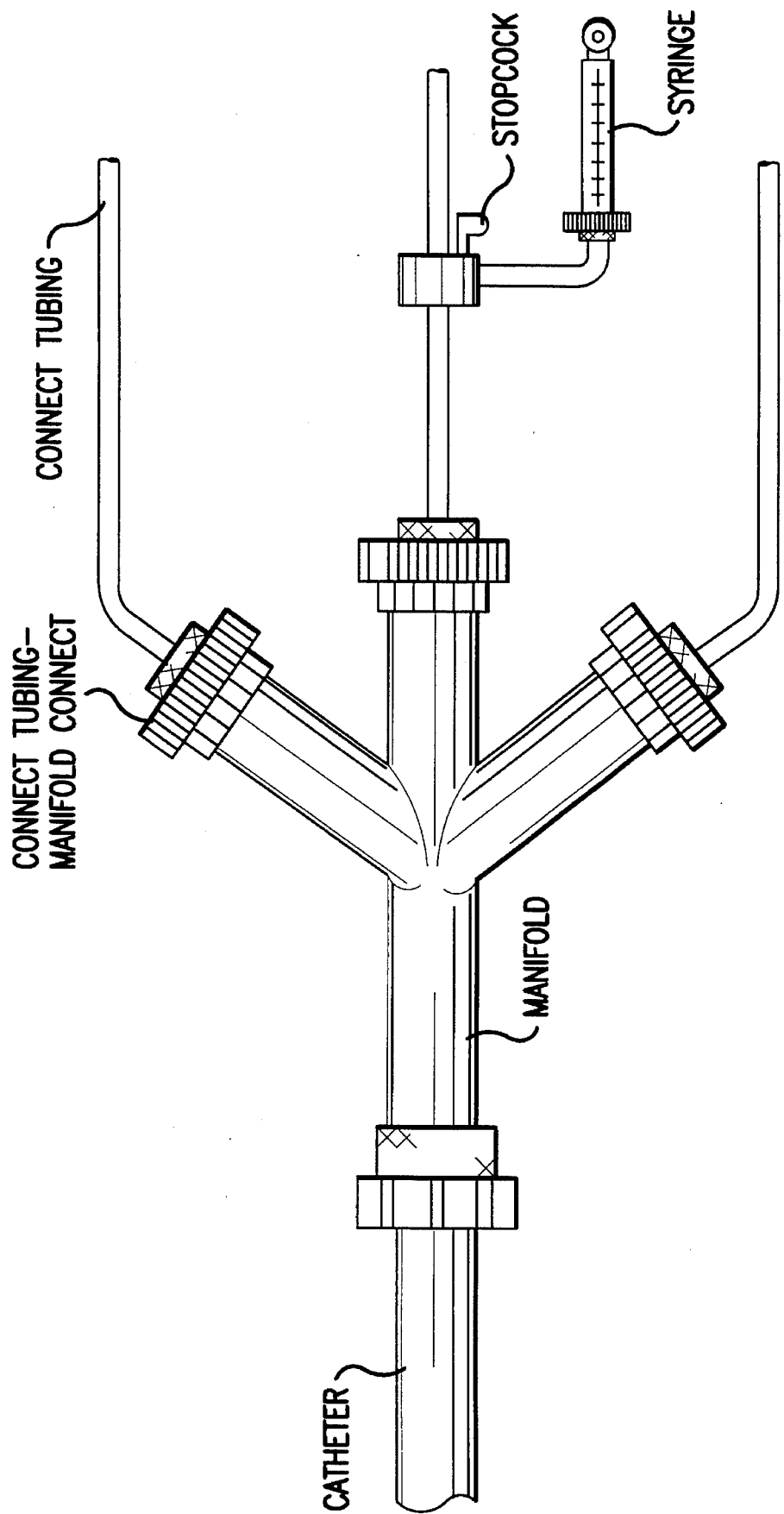
FIG. 4 shows the converging manifold of the invention.
Figure 5:
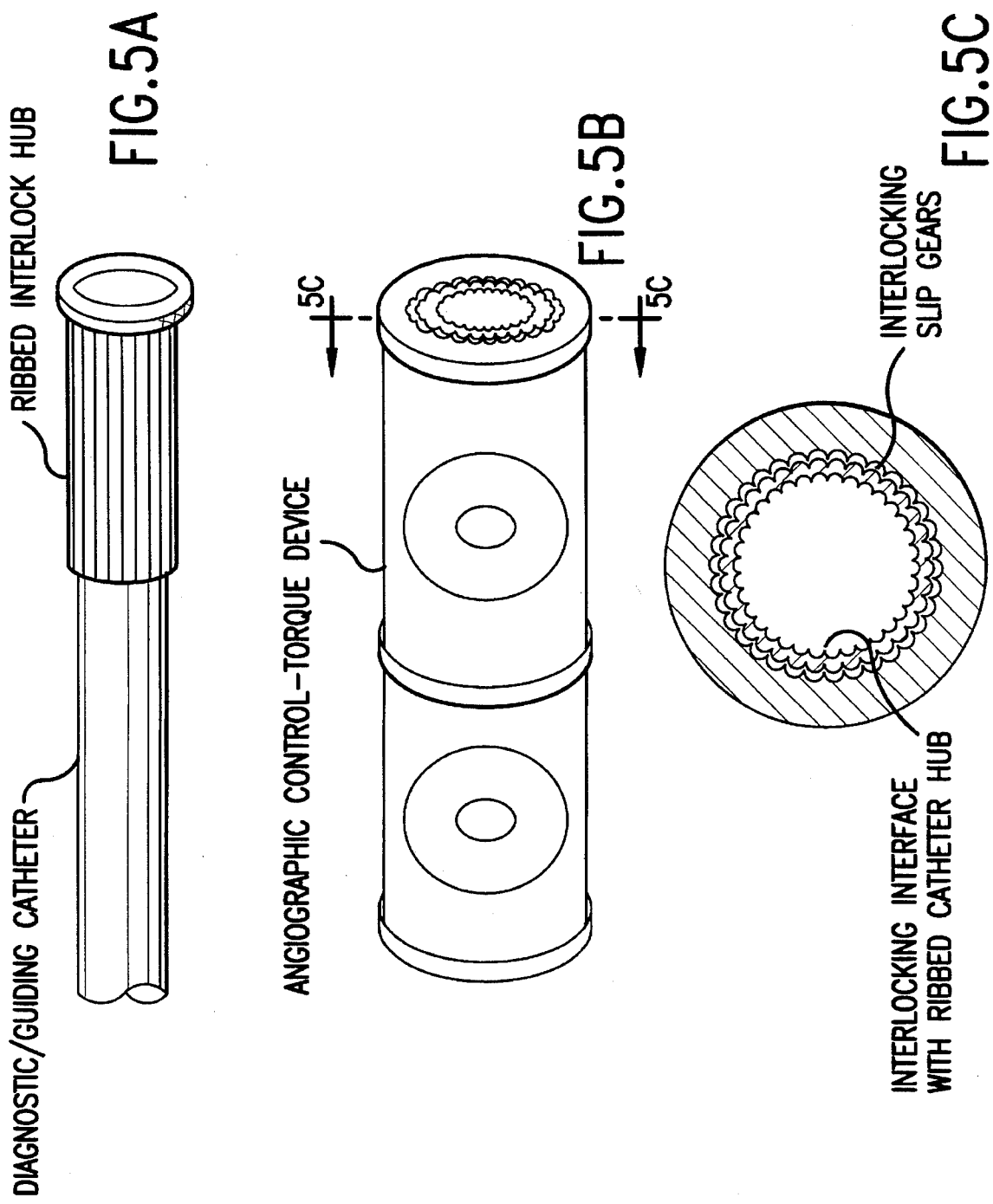
FIG. 5 shows the finger pad torque device of the invention.
Figure 6:
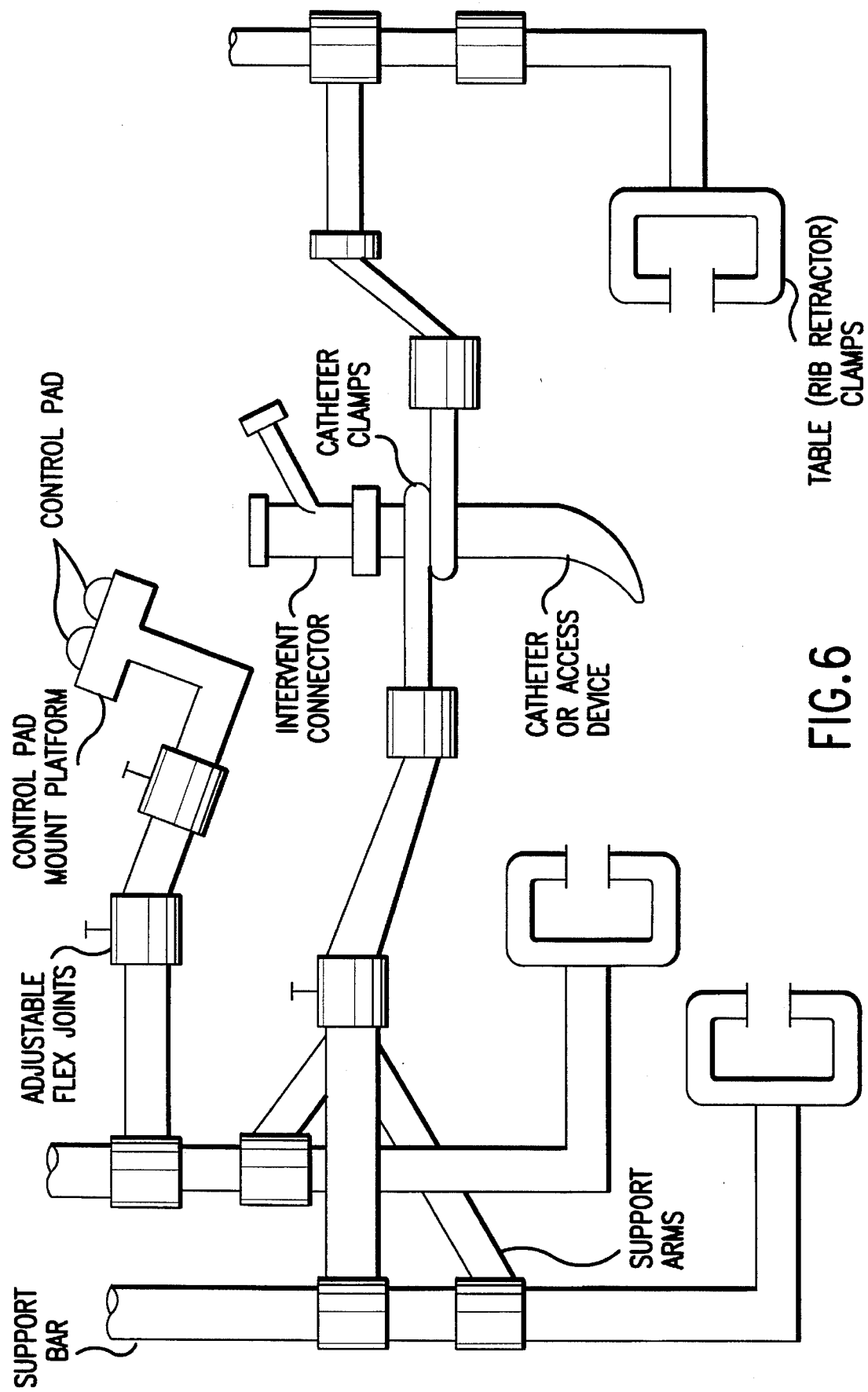
FIG. 6 shows the support system for the invention.

The angiographic control pad system can be deployed in two forms: (a) A clip-on device (FIG. 4) that can be slipped over and secured to the angiographic devices (guiding catheter, balloon dilatation catheter, angiographic manifold or "Y" connector) through a clip-on and cinch-down clamp system that is adjustable. This allows for modulation of position and proximity such that the trigger controls can be accessed by any finger of either hand of the primary operator. (b) This same snap on control pad can alternatively be mounted/attached to a specially designed platform (FIG. 5), which is itself attached to and suspended by an adjustable brace connected to a pole mounted on the operating table. This platform can be adjusted and positioned adjacent to the operator's hands. This control pad platform has a connecting site for the angiographic control pad, as well as similar connection sites for connection, positioning and stabilization of other angiographic devices, such as the guiding catheter, balloon dilatation catheter, manifold, "Y" connector and coronary guide wire. This platform is connected by a multi-jointed flexible arm that is then anchored to the catheterization table by a C-clamp device. This multi-jointed flexible arm facilitates optimal positioning of the control pad platform at any position and height within the operative field.

Equipment Setup and Function Algorithms

The angiographic control pad is connected by cable to the microprocessor. The fluid reservoir syringes are connected to the high pressure sterile disposable plastic connect tubing; the free end of the connect tubing is then passed through the hydraulic occluder cuff; the fluid reservoir is then snapped into and connected to the plunger control system within the fluid reservoir cabinet. The angiographic control pad is then employed to initiate activation of the plunger system to initiate fluid flow through the plastic tubing to flush the system. The plastic connect tubing is then connected to the manifold and, in sequence, each port is flushed by angiographic pad injection control. The manifold is thus prepared for access to the patient via connection of the manifold to the catheter or Y-connecting device. During the procedure, if a fluid reservoir is near depletion, the reservoirs can be replaced in one of several ways: The fluid reservoir can be disconnected from the plunger system and detached (snapped out of) the fluid reservoir cabinet with the tubing intact; the tubing can then be disconnected from the manifold and the reservoir replaced. Alternatively, the connect tubing can be disengaged from the empty fluid reservoir first, a new fluid reservoir attached to the tubing, re-snapped into place and reconnected to the plunger system.

Angiographic injections are controlled as follows: At baseline, following the initial system set up during which the pressure connect tubings, manifold interventional connector and catheter have been properly flushed and cleared of air bubbles, the computer algorithm dictates that the guiding catheter port will be open to the pressure measuring line, whereas the occluders to the saline and contrast dye injection ports will be closed. Activation of the trigger pad for contrast injection will simultaneously activate the occluder to close off the pressure port, as well as release and therefore open the dye injection port; angiographic injections are initiated by subsequent depression of this finger touch button (described below). Release of this trigger will instantaneously reverse the process, with simultaneous occlusion of the contrast injection port and opening of the pressure port. Finger touch activation of the trigger for saline injection will simultaneously close the pressure port and open the saline infusion port; release of this trigger will similarly reverse the process, resulting in hydraulic occlusion closing off the saline infusion port and re-opening of the pressure port line.

This system in aggregate is not limited to only an electrically driven apparatus, but equally applicable to a mechanical non-electric system that similarly allows the operator to simultaneously inject procedure dependent fluids (dye, etc.) while manipulating the primary catheterization equipment (catheters, wires, etc.). This system is not limited to cardiac angiographic procedures only, but is widely applicable to other non-cardiac angiographic applications which similarly require and benefit from simultaneous angiographic equipment manipulation and injection of procedure dependent fluids.

I claim:

1. An angiographic fluid control system which comprises:
   a) a catheter;
   b) at least one fluid reservoir which contains a contrast medium;
   c) a manifold in communication with said catheter and reservoir for passage of said contrast medium;
   d) a pumping device that pumps said contrast medium from said reservoir through said manifold; and
   e) a control unit which communicates with said pumping device wherein said control unit has a communications pad that is adapted to be manually activated by an operator's fingers for the precise pumping of said contrast medium, said communications pad further comprising switches that selectively engage said pumping device.

2. The control system of claim 1 wherein said control unit is mounted onto the catheter.

3. The control system of claim 1 wherein said control unit is mounted on a mechanical arm.

4. The control system of claim 1 wherein said control unit is mechanical.

5. The control system of claim 1 further including a microprocessor wherein said control unit is in communication with the microprocessor.

6. The control system of claim 1 wherein said manifold contains no stopcocks.

7. The control system of claim 1 wherein said control unit is mounted on a platform.

8. The control system of claim 1 wherein said catheter is an angioplasty catheter.

9. The control system of claim 1 wherein said catheter is a vascular access sheath.

* * * * *